| United States Patent [19] | [11] | 4,415,551 |
|---|---|---|
| Fang | [45] | Nov. 15, 1983 |

[54] BIOERODIBLE DEODORANT

[75] Inventor: Florence S. Fang, Bethesda, Md.

[73] Assignee: The Gillette Company, Boston, Mass.

[21] Appl. No.: 344,089

[22] Filed: Jan. 29, 1982

[51] Int. Cl.$^3$ .................. A61K 7/32; A61K 31/74; A61K 31/14

[52] U.S. Cl. .................. 424/65; 424/78; 424/329; 424/330

[58] Field of Search .............. 424/65, 78, 329, 330

[56] References Cited

U.S. PATENT DOCUMENTS

| Re. 29,871 | 12/1978 | Papantoniou | 424/78 |
| 4,090,013 | 5/1978 | Ganslaw et al. | 424/65 |
| 4,240,450 | 12/1980 | Grollier et al. | 424/70 |
| 4,243,548 | 1/1981 | Heeb et al. | 424/DIG. 1 |

OTHER PUBLICATIONS

Sagarin, Cosmetics Science & Technology, 9/1957, pp. 827, 829, 828, 830.

The Merck Index, 9th Edition, 1976, pp. 139 and 254.

*Primary Examiner*—Dale R. Ore
*Attorney, Agent, or Firm*—Leonard J. Janowski

[57] ABSTRACT

This invention relates to bioerodible deodorant formulations for use on the human body employing the controlled release of water-soluble cationic germicides from hydrophobic carboxylic acid polymer matrices. A broad spectrum of germicide release rates is achieved by varying the choices of matrix and germicide and the loading levels.

4 Claims, No Drawings

BIOERODIBLE DEODORANT

BACKGROUND OF THE INVENTION

This invention relates to bioerodible deodorant formulations for use on the human body employing the controlled release of water-soluble cationic germicides from hydrophobic carboxylic acid polymer matrices. A broad spectrum of germicide release rates is achieved by varying the choices of matrix and germicide and the loading levels.

The sustained delivery of drugs and other materials for the treatment of the human body has been a major area of research during recent years. The various types of sustained drug delivery developments can be broadly classified into diffusional, osmotic, and erosional. In the first two of these, the delivery rate of the drug or other treating material is essentially independent of the biological environment and hence can be predicted on theoretical principles. However, unless a diffusional or osmotic delivery system is capable of bioerosion, some means must be provided for its removal once its delivery role has been completed. Since there are applications in which this is not feasible or convenient, there has existed a need for systems that can controllably deliver a treating material by erosion, yielding only toxicologically acceptable degradation products.

One simple approach to a bioerodible delivery system is to disperse or dissolve the material to be delivered in a natural or synthetic water-soluble polymer. Upon dissolution of the polymer in an aqueous medium, the drug or other material is delivered at a rate which can be controlled to some extent by choice of the polymer and treating material. Another approach is to control the dissolution rate of a water-soluble polymer in such a system by the introduction of hydrolyzable chemical cross-links resulting in a hydrophilic gel that slowly erodes as the cross-links are broken. The use, however, of a water-soluble polymer as a major constituent yields a very hydrophilic polymer matrix that will be completely permeated by water leading to leaching of the treating material. In such a system, release of the drug or other treating material from the matrix will be principally determined by drug diffusion and water solubility.

A more desirable approach involves the use of hydrophobic, water-insoluble polymers capable of releasing a treating material by erosion of the matrix with only a minimal amount of release by diffusion. Where the erosion process can be confined to the polymer-water interface and where the total area of the polymer matrix does not significantly change with time, constant or zero order release kinetics can be expected. The delivery rates from such a system can be controlled by simply varying drug loading and/or the matrix erosion rate.

The use of hydrophobic polymers which are solubilized by ionization of a pendent carboxyl group with consequent dissolution and drug release are well known. Among the publications dealing with such systems is U.S. Pat. No. 3,811,444, which describes an ocular insert for the continuously controlled administration of a therapeutically effective dosage of drug to the eye over a prolonged period of time. Also relevant is U.S. Pat. No. 3,608,063 disclosing sustained release pharmaceutical compositions prepared by combining, in the presence of water and a carboxylic acid, a polymer having acidic or basic functionality with a pharmaceutically active material having, respectively, basic or acidic functionality to yield a product having sustained release, enteric, and delayed-release properties.

Although apparently not based upon any sustained release capability of the compositions described, U.S. Pat. No. 3,956,480 is relevant in that it describes a treatment of teeth by the sorption onto tooth surfaces of a combination of a cationic germicide and an anionic polymer. Relevant, because of its cosmetic application, is the teaching of South African Pat. No. 751473 which discloses antiperspirant compositions containing as an ingredient a perspiration-absorbing polymer such as a copolymer of polyvinylmethylether and maleic anhydride. The compositions may contain, as an additional ingredient, a variety of germicides. There is no teaching with respect to any sustained release properties inherent in the compositions.

OBJECTS OF THE INVENTION

It is a primary object of this invention to provide a bioerodible deodorant composition capable of dispensing a germicide to the human skin in a controlled and continuous fashion.

Another object of the invention is to provide a bioerodible deodorant composition capable of providing a uniform sustained rate of release of germicide in cosmetically effective amounts.

A still further object of the invention is to provide a deodorant comprising a bioerodible material associated with a germicide having a relatively high solubility in human perspiration.

These objects as well as other objects, features, and advantages will become more readily apparent from the following detailed description.

DETAILED DESCRIPTION OF THE INVENTION

Conventional, germicidal deodorant formulations have limited efficacy because the germicidally active agent, typically a quaternary ammonium compound, is usually water soluble and removed from the treatment site by the action of normal perspiration. To overcome this short-lived activity, I employ a sustained release formulation in which a quaternary ammonium germicidal material is formulated together with a hydrophobic carboxylic polymer to form, upon application, a matrix capable of releasing the germicide at a rate high enough to provide deodorant capability without the risk of causing skin irritation by the effects of too high a concentration of the germicide.

Suitable carboxylic polymers are the hydrophobic polyacids which are represented by the general formula:

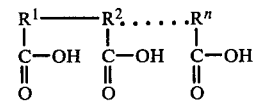

wherein:

the R's are organic radicals independently selected to provide an average of from eight to 22 total carbon atoms for each acidic carboxylic hydrogen. Variations of the ratio within this range can vary the matrix erosion and germicide release rates of deodorant compositions containing these polymeric acids. Organic radicals represented by $R^1$, $R^2$,-$R^n$ may be selected from hydrocarbon radicals and hetero-atom containing organic radicals. Suitable hetero-atoms for employment in $R^1$, $R^2,-R^n$ include oxygen, nitrogen, sulfur and phosphorous as well as other hetero-atoms so long as the required hydrophobicity and carbon to carboxylic hydrogen average ratio is maintained. The value of n and hence the average molecular weight of the polymer is not critical and may vary over a wide range. Suitable molecular weights, for example, range from about 10,000 to about 800,000. Materials within this range bioerode to products which may be easily removed from the skin while bathing or showering. Preferred molecular weights are from about 15,000 to 500,000.

A detailed description of the preparation of various types of carboxylic polymers within the above generic definition can be found in U.S. Pat. No. 3,811,444 which, for that purpose, is incorporated herein by reference.

A group of carboxylic polymers preferred for use in accordance with the present invention comprise hydrophobic copolymers of maleic acid with about one mole, per mole of maleic acid, of ethylene or an alkylvinyl ether in which the alkyl group contains 1 to 2 carbon atoms, said copolymers having about half of their total carboxyl groups esterified with a lower monoalcohol having from 2 to 4 carbon atoms, wherein the carbon to acidic carboxylic hydrogen ratio has a value of from about 9:1 to about 12:1.

Quaternary ammonium germicidal materials useful for cosmetic deodorant purposes are well known in the art. See, for example, the section entitled "Quaternary Ammonium and Related Compounds" in the article on "Antiseptics and Disinfectants" in Kirk-Othmer Encyclopedia of Chemical Technology, Second Edition (Volume 2, pages 632–635), which is incorporated herein by reference. Among the more common of these materials are the following.

I. ALIPHATIC AND AROMATIC QUATERNARY AMMONIUM COMPOUNDS

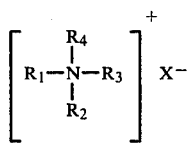

where $R_1$, $R_2$, $R_3$, and $R_4$ are aliphatic or aromatic side chains having 1 to 18 carbon atoms at least one of which has 8 to 18 carbon atoms and in which X is selected from hydroxide, chloride, bromide, or methyl sulfate.

II. PYRIDINIUM COMPOUNDS

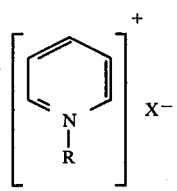

where R is an alkyl group having from 8 to 18 carbon atoms and X is selected from hydroxide, chloride, bromide, or methyl sulfate.

III. ISOQUINOLINIUM COMPOUNDS

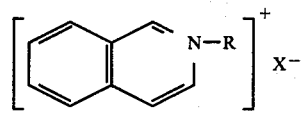

where R is an alkyl group having 8 to 18 carbon atoms and X is selected from hydroxide, chloride, bromide, or methyl sulfate.

IV. MORPHOLINIUM COMPOUND

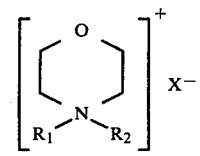

where $R_1$ and $R_2$ are alkyl side chains having from 1 to 18 carbon atoms at least one of which has 8 to 18 carbon atoms, and X is selected from hydroxide, chloride, bromide, or methyl sulfate.

V. IMIDAZOLINIUM COMPOUNDS

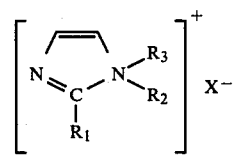

where $R_1$, $R_2$, and $R_3$ are aliphatic or aromatic side chains having from 1 to 18 carbon atoms at least one of which has 8 to 18 carbon atoms, and X is selected from hydroxide, chloride, bromide, or methyl sulfate.

VI. BIS OR POLYQUATERNARY AMMONIUM COMPOUNDS

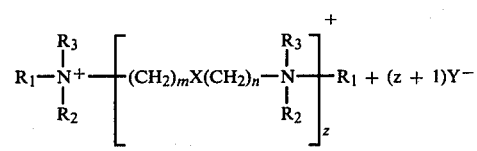

where $R_1$, $R_2$, and $R_3$ are alkyl side chains having 1 to 18 carbon atoms at least one of which has 8 to 18 carbon atoms; in which X is a methylene, thioether, or an ether linkage; and in which Y is selected from hydroxide, chloride, bromide, or methyl sulfate and in which m and n are integers of 1–6 and z is an integer of 1–10.

In formulating the sustained release germicidal deodorant compositions of this invention, the choice of carboxylic polymer, species of quaternary ammonium germicide, and the proportions of the two will all play a role in controlling the rate at which the active germicidal species is released by bioerosion of the matrix in vivo. Since the preferred compositions of this invention are in the form of essentially non-aqueous solutions containing both the carboxylic polymer and quaternary ammonium germicide, it is theorized that when the natural skin moisture and pH conditions cause the carboxylic acid to ionize, the partially ionized polymer interacts with the quaternary ammonium compound, resulting in a matrix with a much reduced rate of bioerosion, which, in turn, provides the release of an optimum level of the quaternary germicide. The germicide release and polymer film dissolution are concomitant, suggesting negligible diffusional release of the germicide. It is of particular importance to note that the incorporation of a water soluble active agent other than the quaternary ammonium compounds results in no or at best weak interactions, which do not significantly alter the rate of bioerosion of the polymer matrix.

I have found that the hydrophobicity of the matrix and hence resistance to bioerosion increases as the proportion of germicidal species to carboxylic polymer increases. As the proportion of germicide increases beyond a certain point which is dependent upon the particular chemical species involved, the film becomes increasingly hydrophilic and the water soluble germicide is readily leached out by the water from perspiration.

Where more hydrophobic polymer and germicidal species are formulated together to form a relatively more hydrophobic matrix, it is usually advantageous to work at lower proportions of germicide to polymer since compositions which are higher in germicide-to-polymer ratio may bioerode at a rate such that the amount of germicide released over a given period of time will be less than is desirable for the control of perspiration odor.

In like manner where relatively less hydrophobic polymer and germicidal species are employed, it will usually be preferable to employ them at the upper end of the ratio of polymer-to-germicide to insure that bioerosion with consequent germicidal release does not proceed at too great a rate, possibly leading to dermal irritation. Taking the above principles into consideration, I have found that compositions capable of bioeroding to release germicidal species within the useful range of rates can be formulated by using polymer-to-germicide molar ratios of from 13:1 to 1:1.

The amount of active germicidal species that is released in vivo is a function not only of the rate of release as discussed above, but also a function of the total quantity of matrix, i.e. film thickness, present on the skin. I have found that as little as 2% by weight of the combination of carboxylic polymer and germicide can be present in the non-aqueous composition which is applied to the skin while as much as 20% by weight can be employed where formulation considerations and product aesthetics permit. We prefer to use from 5 to 15% by weight.

An especially preferred form of the invention involves the use of mixtures of two or more germicidal species of varying hydrophobicity to provide a system giving an intermediate germicide release rate and the benefit of two active agents which may have different activity profiles.

As mentioned above, it is necessary to formulate the carboxylic polymer and quaternary ammonium germicide ingredients together in an essentially non-aqueous system to prevent the precipitation of the hydrophobic polymer. In their simplest form, the compositions of this invention comprise a 2–20% solution of polymer and germicide in a cosmetically acceptable nonaqueous organic solvent such as ethanol. Other solvents that may be employed either alone or in admixture include isopropanol and acetone. In any case, the amount of water present in such compositions should not exceed 10% by weight.

The formulated solutions of this invention may be packaged for application in any of the conventional ways in which cosmetic solution have been packaged for application to the human body in the past. These include roll-on applicators, dab-on systems, and spray application from either unpressurized pump or squeeze containers or from pressurized aerosols. Since the details of these forms of packaging are well known to the art, it not necessary to describe them in greater detail herein.

EXAMPLES

EXAMPLE I

For the purpose of determining in vitro polymer dissolution and germicide release rates of a carboxylic polymer in combination with a quaternary ammonium germicidal material, the following composition was prepared.

| Ingredient | Weight/Volume |
| --- | --- |
| Ethyl half-ester of poly(methyl vinyl ether/maleic acid) (GANTREZ ES-225; GAF Corporation) | 7.5 g |
| Diisobutylphenoxyethoxyethyl dimethyl benzyl ammonium chloride monohydrate (HYAMINE 1622; Rohm & Haas) | 2.5 g |
| Ethyl alcohol | to 100 ml |

A polymer film of the above composition was prepared by pipetting a calculated volume of solution onto a glass plate and allowing alcohol to evaporate.

Polymer dissolution rate was determined by weighing samples of the film before and after immersion under controlled conditions in a synthetic perspiration solution formulated to have the same pH and buffering capacity as physiologically produced perspiration. Release rate of the active ingredient in the film was determined by periodically sampling the solution in which the film was immersed and measuring the quaternary ammonium germicide spectrophotometrically.

After one hour of immersion, approximately 18% by weight of the film had dissolved and 22% of the germicide had been released. After five hours of immersion, approximately 70% by weight of the film had dissolved and 68% of the germicide had been released.

EXAMPLE II

For the purpose of comparing the in vitro dissolution rates of a carboxylic polymer of the type employed in the practice of this invention both in the absence of and in combination with a quaternary ammonium germicidal material, the following composition was prepared.

| Ingredient | Weight/Volume |
| --- | --- |
| Ethyl half-ester of poly(methyl vinyl ether/maleic acid) (GANTREZ ES-225; GAF Corporation) | 7.5 g |
| Diisobutylphenoxyethoxyethyl dimethyl benzyl | 2.5 g |

| Ingredient | Weight/Volume |
|---|---|
| ammonium chloride monohydrate (HYAMINE 1622; Rohm & Haas) | |
| Ethyl alcohol | to 100 ml |

A polymer film of the above composition was prepared by pipetting a calculated volume of solution onto a glass plate and allowing alcohol to evaporate. A similar polymer film was prepared from a simple ethanol solution of GANTREZ ES-225.

Using the film dissolution technique described in Example I, the following observations were made. After one-half hour of immersion, approximately 96% by weight of the film containing GANTREZ ES-225 alone had dissolved while only 15% of the film containing both GANTREZ and HYAMINE 1622 had dissolved. After four hours, the GANTREZ film had essentially completely dissolved while about 35% of the combination film remained undissolved.

EXAMPLE III

For the purpose of comparing the relative in vitro dissolution rate of carboxylic polymers having different levels of hydrophobicity, the following composition was prepared.

| Ingredient | Weight/Volume |
|---|---|
| GANTREZ ES-225 | 7.5 g |
| HYAMINE 1622 | 2.5 g |
| Ethyl alcohol | to 100 ml |

A similar composition substituting the butyl half-ester of poly(methyl vinyl ether/maleic anhydride) (GANTREZ ES-425; GAF Corporation) for the ethyl half-ester was also prepared.

Measurement of the relative release rates using prepared films and a synthetic sweat solution as described in Example I showed the following result. After five hours, the film containing the more hydrophobic butyl ester had released only about 28% of the total germicide present while the less hydrophobic ethyl ester had released about 74% of the total germicide.

EXAMPLE IV

For the purpose of comparing the release rates of quaternary ammonium germicides having varying levels of hydrophobicity, the following composition was prepared.

| Ingredient | Weight/Volume |
|---|---|
| GANTREZ ES-225 | 8.5 g |
| 1-hexadecylpyridinium chloride | 1.5 g |
| Ethyl alcohol | to 100 ml |

A similar composition substituting an n-alkyl (50% $C_{14}$, 40% $C_{12}$, 10% $C_{16}$) dimethyl benzyl ammonium chloride (HYAMINE 3500; Rohm & Haas) for the 1-hexadecylpyridinium chloride was also prepared.

Using the release rate studies described in Example I, the following observations were made. Within about two and one-half hours, essentially all of the 1-hexadecylpyridinium chloride had been released from the polymer matrix while only about 30% of the more hydrophobic HYAMINE 3500 had been released. Even after 15 hours, more than 10% of the bound HYAMINE 3500 remained to be released.

EXAMPLE V

For the purpose of making an in vitro study of the release rates of a carboxylic polymer combined with a mixture of two quaternary ammonium germicides, the following composition was prepared.

| Ingredient | Weight/Volume |
|---|---|
| GANTREZ ES-225 | 7.5 g |
| HYAMINE 1622 | 2.0 g |
| 1-hexadecylpyridinium chloride | 0.5 g |
| Ethanol | to 100 ml |

Similar compositions containing equivalent quantities of either 1-hexadecylpyridinium chloride or HYAMINE 1622 as the only germicides present were also prepared. Employing release rate studies of the type described in Example I, the following observations were made.

The release rate of germicide from the film containing the 1-hexadecylpyridinium chloride was extremely rapid with essentially all of the germicide having been released within about two hours. In contrast, the more hydrophobic HYAMINE 1622 was released from its film substantially more slowly with about 20% of the total germicide still remaining after about 13 hours. The film containing the mixture of germicides behaved in an intermediate fashion with 80% of the total germicide being released within about five hours.

EXAMPLE VI

To illustrate the use of mixed carboxylic polymer systems in controlling the rate of germicide release, the following four compositions were prepared.

| Ingredient | Weight/Volume |
|---|---|
| GANTREZ ES-225 | 7.5 g |
| HYAMINE 1622 | 2.5 g |
| Ethyl alcohol | to 100 ml |
| GANTREZ ES-225 | 5.625 g |
| GANTREZ ES-425 | 1.875 g |
| HYAMINE 1622 | 2.5 g |
| Ethyl alcohol | to 100 ml |
| GANTREZ ES-225 | 5.625 g |
| 1:1 copolymer of methyl methacrylate and methacrylic acid | 1.875 g |
| HYAMINE 1622 | 2.5 g |
| Ethyl alcohol | to 100 ml |
| GANTREZ ES-225 | 5.625 g |
| 3:1 copolymer of methyl methacrylate and methacrylic acid | 1.875 g |
| HYAMINE 1622 | 2.5 g |
| Ethyl alcohol | to 100 ml |

All four compositions were compared employing release rate studies as described in Example I. After five hours, almost 75% of the HYAMINE 1622 had been released from the least hydrophobic polymer, the GANTREZ ES-225, while about 39% had been released from the most hydrophobic polymer, the mixture of GANTREZ ES-225 and the 3:1 copolymer of methyl methacrylate and methacrylic acid. The other two compositions released the HYAMINE 1622 at an intermediate rate with about 51% having been released at the end of five hours. At the end of 15 hours, about 95% of the germicide had been released from the least hydrophobic film while about 55% had been released from the most hydrophobic film. Again, the other two compositions were intermediate, having released about 60% of the available HYAMINE 1622.

EXAMPLE VII

An axillary recovery study was conducted to compare the residence time of a test formulation of this invention with a conventional deodorant formulation in the form of an aerosol package containing 0.2% HYAMINE 1622 and ethyl alcohol. Six hours after application, approximately 40% of the test formulations still remain in the axiallae compared to only about 15% of the control formulation.

EXAMPLE VIII

An in vivo deodorant study was conducted by applying 0.5 ml of an ethanolic solution containing 7.5% by weight of GANTREZ ES-225 and 2.5% of HYAMINE 1622. Axillary odor results of the test composition and the conventional aerosol deodorant formulation described in Example VI were scored by trained odor judges using a paired comparison method. The test composition was determined to be significantly more effective, confirming that a controlled release formulation containing HYAMINE 1622 is more efficacious than a conventional formulation.

While particular embodiments of the invention have been described, it will be apparent to those skilled in the art that variations may be made thereto without departing from the spirit of the invention and the scope of the appended claims.

What is claimed is:

1. A sustained release bioerodible deodorant formulation for use on the human body consisting essentially of a cosmetically acceptable, non aqueous organic solvent solution containing 2 to 20% by weight of a mixture of a quaternary ammonium germicidal material and a carboxylic polymer having the general formula:

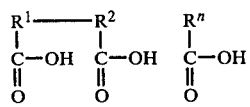

in which $R^1$, $R^2$,-$R^n$ are organic radicals selected from the group consisting of hydrocarbon radicals and hetero-atom containing radicals, in which the R's are selected to provide an average of from 8 to 22 carbon atoms for each acidic carboxylic hydrogen and in which the value of n is selected to provide a molecular weight of about 10,000 to 800,000; the molar ratio of said carboxylic polymer to said germicidal material being from about 13:1 to 1:1.

2. A sustained release bioerodible deodorant formulation as described in claim 1 in which said carboxylic polymer is selected from the group consisting of hydrophobic copolymers of maleic acid with about 1 mole, per mole of maleic acid, of ethylene or an alkylvinyl ether in which the alkyl group contains 1 to 2 carbon atoms, said copolymers having about half of their total carboxyl groups esterified with a lower monoalcohol having from 2 to 4 carbon atoms and in which the carbon to acidic carboxylic hydrogen ratio has a value of from 9:1 to 12:1, the molecular weight of said carboxylic polymer being about 15,000 to 500,000.

3. A sustained release bioerodible deodorant formulation as described in claim 1 in which the germicidal material comprises a mixture of species of varying hydrophobicity.

4. A sustained release bioerodible deodorant formulation as described in claim 1 in which the germicidal material is selected from the group consisting of 1-hexadecylpyridinium chloride and compounds having the general formula

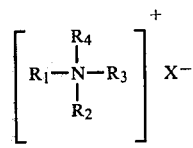

in which $R_1$, $R_2$, $R_3$, and $R_4$ are aliphatic or aromatic side chains having 1 to 18 carbon atoms at least one of which has 8 to 18 carbon atoms and in which X is selected from hydroxide, chloride, bromide and methyl sulfate.

* * * * *

UNITED STATES PATENT AND TRADEMARK OFFICE
CERTIFICATE OF CORRECTION

PATENT NO. : 4,415,551
DATED : November 15, 1983
INVENTOR(S) : Florence S. Fang

It is certified that error appears in the above—identified patent and that said Letters Patent are hereby corrected as shown below:

Col. 2, line 67, " $-R^n$ " should be -- $\ldots R^n$ --;

Col. 3, line 2, " $-R^n$ " should be -- $\ldots R^n$ --;

Col. 6, line 5, "solution" should be -- solutions --;

Col. 10, line 1, " $R^1 \text{_____} R^2 \quad R^n$ " should be -- $R^1 \text{_____} R^2 \ldots R^n$ --

Signed and Sealed this

*Fourteenth* Day of *February 1984*

[SEAL]

*Attest:*

GERALD J. MOSSINGHOFF

*Attesting Officer*  *Commissioner of Patents and Trademarks*